(12) United States Patent
Zullo

(10) Patent No.: US 12,371,715 B2
(45) Date of Patent: Jul. 29, 2025

(54) PROCESSES AND SYSTEMS TO PRODUCE RENEWABLE ENERGY AND FIBER FROM CELLULOSE-RICH WASTE MATERIALS

(71) Applicant: BurCell Technologies, Inc., Kennesaw, GA (US)

(72) Inventor: Luca Zullo, Excelsior, MN (US)

(73) Assignee: BurCell Technologies, Inc., Kennesaw, GA (US)

( * ) Notice: Subject to any disclaimer, the term of this patent is extended or adjusted under 35 U.S.C. 154(b) by 0 days.

(21) Appl. No.: 18/648,034

(22) Filed: Apr. 26, 2024

(65) Prior Publication Data
US 2024/0360483 A1 Oct. 31, 2024

Related U.S. Application Data

(60) Provisional application No. 63/462,554, filed on Apr. 28, 2023.

(51) Int. Cl.
| | |
|---|---|
| *C12P 5/02* | (2006.01) |
| *C12M 1/00* | (2006.01) |
| *C12M 1/33* | (2006.01) |
| *C12P 19/14* | (2006.01) |
| *C13K 1/02* | (2006.01) |

(52) U.S. Cl.
CPC ............ *C12P 5/023* (2013.01); *C12M 45/02* (2013.01); *C12M 45/05* (2013.01); *C12M 45/07* (2013.01); *C12P 19/14* (2013.01); *C13K 1/02* (2013.01); *C12P 2201/00* (2013.01); *C12P 2203/00* (2013.01)

(58) Field of Classification Search
CPC ....... C12P 5/023; C12P 19/14; C12P 2201/00; C12P 2203/00; C12M 45/02; C12M 45/05; C12M 45/07; C12M 45/20; C13K 1/02
See application file for complete search history.

(56) References Cited

U.S. PATENT DOCUMENTS

| | | |
|---|---|---|
| 2008/0257888 A1 | 10/2008 | Lee |
| 2009/0120778 A1 | 5/2009 | Vanderpool |
| 2012/0104313 A1 | 5/2012 | Garbero et al. |
| 2013/0065289 A1 | 3/2013 | Carlson |
| 2016/0186072 A1 | 6/2016 | Lehoux et al. |

OTHER PUBLICATIONS

International Search Report and Written Opinion, PCT/US2024/026694, dated Jun. 21, 2024.

*Primary Examiner* — Iqbal H Chowdhury
(74) *Attorney, Agent, or Firm* — O'Connor & Company; Ryan P. O'Connor

(57) ABSTRACT

Some variations provide a process to produce renewable biogas and cellulosic fiber from a cellulose-rich feedstock, comprising: obtaining a cellulose-rich feedstock that is reduced in concentration of impurities and has a length less than 5 inches; feeding the cellulose-rich feedstock and water to a vacuum steam-explosion vessel, thereby generating a first cellulose-rich intermediate stream; feeding the cellulose-rich intermediate stream to a secondary separation vessel to remove remaining impurities, thereby generating a second cellulose-rich intermediate stream; feeding the second cellulose-rich intermediate stream to an enzymatic-hydrolysis vessel to convert the second cellulose-rich intermediate stream to low-viscosity cellulosic fibers comprising cellulose oligomers; feeding the low-viscosity cellulosic fibers to an anaerobic digester, thereby generating a biogas stream and residual fiber; optionally, recycling residual fiber to the enzymatic-hydrolysis vessel and/or to the anaerobic digester; and recovering some or all of the residual cellulosic fiber from the solid stream as a co-product.

36 Claims, 1 Drawing Sheet

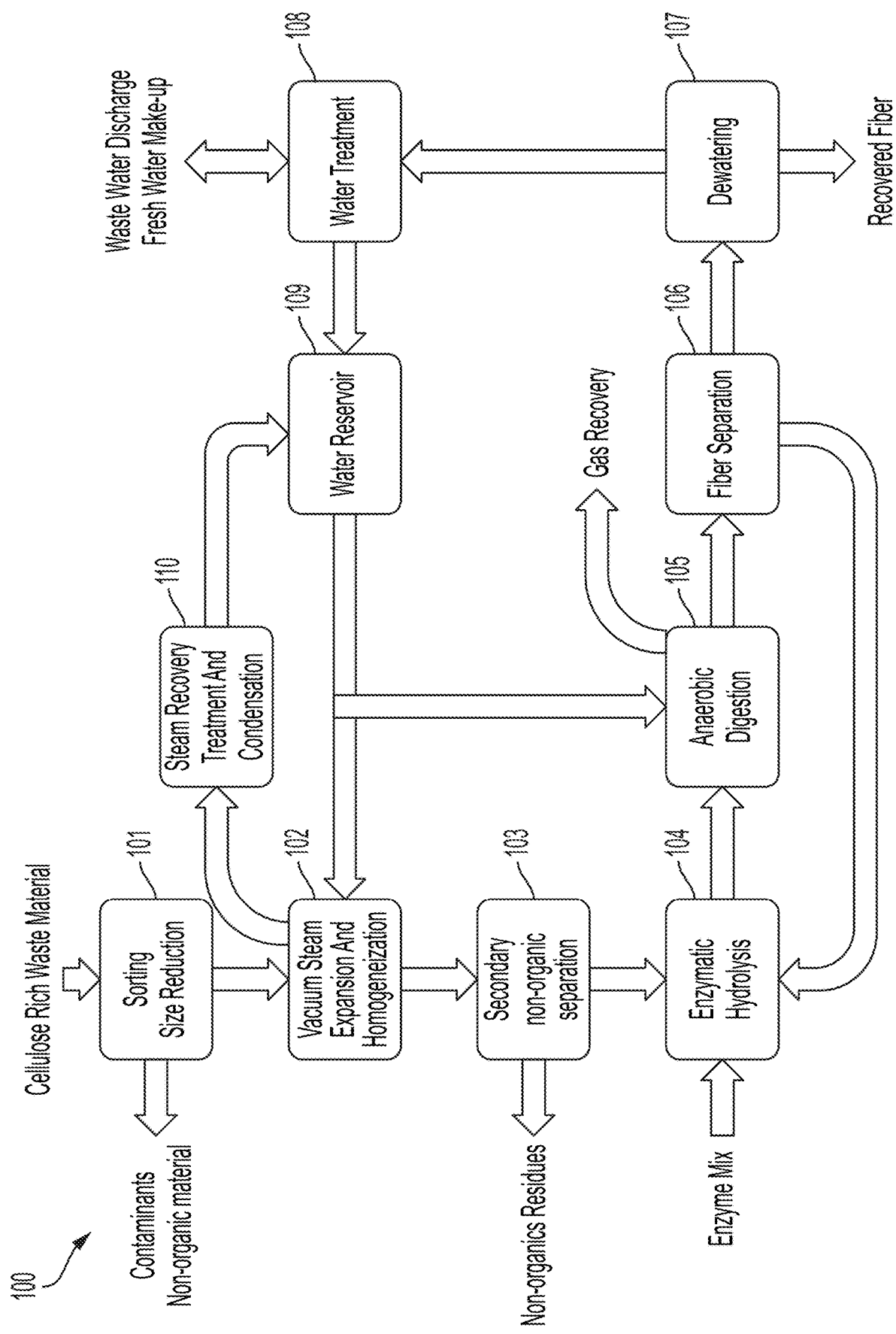

PROCESSES AND SYSTEMS TO PRODUCE RENEWABLE ENERGY AND FIBER FROM CELLULOSE-RICH WASTE MATERIALS

PRIORITY DATA

This patent application claims priority to U.S. Provisional Patent App. No. 63/462,554, filed on Apr. 28, 2023, which is hereby incorporated by reference.

FIELD

The present invention generally relates to anaerobic digestion of pretreated cellulose-rich organic waste materials, and production of fiber co-products.

BACKGROUND

Anaerobic digestion is a series of biological processes in which microorganisms break down biodegradable material in the absence of oxygen. One of the end products is biogas, which may be combusted to generate electricity and heat, or processed into renewable natural gas, transportation fuels, or chemicals. Known anaerobic digestion technologies can convert livestock manure, municipal wastewater solids, food waste, industrial wastewater residuals, fats, oils, grease, and various other organic waste streams into biogas. Separated digested solids can be composted, utilized for dairy bedding, directly applied to cropland, or potentially converted into other products.

The conventional digestion process begins with bacterial hydrolysis of the input materials in order to break down insoluble organic polymers such as carbohydrates and make them available for other bacteria. Acidogenic bacteria then convert the sugars and amino acids into carbon dioxide, hydrogen, ammonia, and organic acids. Acetogenic bacteria convert the organic acids into acetic acid, along with additional ammonia, hydrogen, and carbon dioxide. Finally, methanogens convert these products to methane and carbon dioxide.

Improvements to anaerobic digestion are still desired in order to economically convert waste cellulose-rich streams to biogas, and to generate high-value co-products in addition to the biogas.

SUMMARY

Some variations of the invention provide a process to produce renewable biogas and cellulosic fiber from a cellulose-rich feedstock, the process comprising:
(a) obtaining a cellulose-rich feedstock that is reduced in concentration of impurities, wherein the impurities comprise metals, plastics, glass, dirt, sand, and grit, and wherein the cellulose-rich feedstock is characterized by an average maximum length scale less than 5 inches;
(b) feeding the cellulose-rich feedstock and water to a vacuum steam-explosion vessel, wherein the cellulose-rich feedstock and the water are mixed within the vacuum steam-explosion vessel, wherein a rapid depressurization takes place via vacuum applied to the vacuum steam-explosion vessel, and wherein at least a portion of the water is removed as extracted vapor out of the vacuum steam-explosion vessel via vacuum drying, thereby generating a first cellulose-rich intermediate stream;
(c) feeding the cellulose-rich intermediate stream to a secondary separation vessel to remove at least 50 wt % of the remainder of the impurities present, thereby generating a second cellulose-rich intermediate stream;
(d) feeding the second cellulose-rich intermediate stream to an enzymatic-hydrolysis vessel operated under effective hydrolysis conditions and in the presence of cellulase enzymes to convert the second cellulose-rich intermediate stream to low-viscosity cellulosic fibers comprising cellulose oligomers;
(e) feeding the low-viscosity cellulosic fibers to an anaerobic digester operated under effective digestion conditions and in the presence of microorganisms capable of fermenting the low-viscosity cellulosic fibers to biomethane, thereby generating a biogas stream comprising the biomethane and a solid stream comprising residual fiber;
(f) optionally, recycling a portion of the residual fiber to the enzymatic-hydrolysis vessel and/or to the anaerobic digester; and
(g) recovering some or all of the residual fiber from the solid stream as a co-product comprising the cellulosic fiber.

In some embodiments, step (a) comprises size reduction of the cellulose-rich feedstock.

In some embodiments, step (a) comprises removal metals from the cellulose-rich feedstock via magnetic separation and/or eddy-current separation.

In some embodiments, step (a) comprises optical screening to remove plastics from the cellulose-rich feedstock.

In some embodiments, step (a) comprises gravimetric screening to remove dirt, grit, and sand from the cellulose-rich feedstock.

In some embodiments, in step (b), the water is preheated prior to being added to the vacuum steam-explosion vessel.

The vacuum steam-explosion vessel may be a heated rotary reactor, for example. The vacuum steam-explosion vessel may contain an internal mixer. The vacuum steam-explosion vessel may be mixed via conveyance (e.g., internal agitation) of contents therein. The vacuum steam-explosion vessel may be mixed via rotation of the vacuum steam-explosion vessel. The vacuum steam-explosion vessel may be operated continuously, semi-continuously, or batchwise.

In some embodiments, the process further comprises removing contaminants from the extracted vapor, or a condensed form thereof, using activated carbon. In these or other embodiments, the process further comprises removing contaminants from the extracted vapor, or a condensed form thereof, using an absorption resin. The extracted vapor is removed out of the vacuum steam-explosion vessel during step (b).

In some embodiments, step (c) removes at least 75% of the remainder of the impurities present. In certain embodiments, step (c) removes at least 90% of the remainder of the impurities present.

In some embodiments, in step (d), the enzymatic-hydrolysis vessel is operated in the presence of lipase enzymes and/or amylase enzymes, in addition to the cellulase enzymes.

In some embodiments, in step (d), there is less than 10%, less than 5%, or less than 1% conversion of the second cellulose-rich intermediate stream to glucose. By limiting the enzymatic hydrolysis of the second cellulose-rich intermediate stream such that the hydrolysis does not significantly proceed all the way to glucose monomers, and makes cellulose oligomers instead, the fiber co-production potential is higher, and enzyme costs are reduced.

In some embodiments, the low-viscosity cellulosic fibers are characterized by a viscosity less than 10 Pa·s measured at a temperature of 25° C. and a moisture of 70 wt % $H_2O$.

In some embodiments, step (g) further comprises dewatering the solid stream to generate dirty water. Dewatering may utilize a centrifuge, a rotary vacuum system, a filter press, or a combination thereof, for example.

The dirty water may be treated in a wastewater treatment unit to generate wastewater discharge and cleaned water. In some embodiments, the wastewater treatment unit removes dissolved organic compounds. In some embodiments, the wastewater treatment unit removes dissolved perfluorinated and polyfluorinated substances (PFAS). In some embodiments, the wastewater treatment unit removes dissolved salts. The cleaned water may be fed back to the vacuum steam-explosion vessel as at least a portion of the water required in step (b), i.e., steam is made from the cleaned water for use in the vacuum steam-explosion vessel.

In certain embodiments, the cleaned water and a condensed form of the extracted vapor from step (b) are both fed to a water reservoir. Recycle water from the water reservoir may be fed back to the vacuum steam-explosion vessel as at least a portion of the water for the steam requirement in that vessel.

In some embodiments, the process further comprises combusting or partially oxidizing the biogas to generate renewable energy.

In some embodiments, the process further comprises combusting and biogas to generate heat, and using the heat to generate steam for powering a turbine to generate renewable electricity.

The cellulosic fiber co-product has many potential uses. In some embodiments, the process further comprises incorporating the cellulosic fiber in a biocomposite material. In these or other embodiments, the process further comprises incorporating the cellulosic fiber into a low-carbon-intensity solid-fuel pellet or briquette.

Other variations provide a cellulosic fiber product produced by a process comprising:
(a) obtaining a cellulose-rich feedstock that is reduced in concentration of impurities, wherein the impurities comprise metals, plastics, glass, dirt, sand, and grit, and wherein the cellulose-rich feedstock is characterized by an average maximum length scale less than 3 inches;
(b) feeding the cellulose-rich feedstock and water to a vacuum steam-explosion vessel, wherein the cellulose-rich feedstock and the water are mixed within the vacuum steam-explosion vessel, wherein a rapid depressurization takes place via vacuum applied to the vacuum steam-explosion vessel, and wherein at least a portion of the water is removed as extracted vapor out of the vacuum steam-explosion vessel via vacuum drying, thereby generating a first cellulose-rich intermediate stream;
(c) feeding the cellulose-rich intermediate stream to a secondary separation vessel to remove at least 50 wt % of the remainder of the impurities present, thereby generating a second cellulose-rich intermediate stream;
(d) feeding the second cellulose-rich intermediate stream to an enzymatic-hydrolysis vessel operated under effective hydrolysis conditions and in the presence of cellulase enzymes to convert the second cellulose-rich intermediate stream to low-viscosity cellulosic fibers comprising cellulose oligomers;
(e) feeding the low-viscosity cellulosic fibers to an anaerobic digester operated under effective digestion conditions and in the presence of microorganisms capable of fermenting the low-viscosity cellulosic fibers to biomethane, thereby generating a biogas stream comprising the biomethane and a solid stream comprising residual fiber;
(f) optionally, recycling a portion of the residual fiber to the enzymatic-hydrolysis vessel and/or to the anaerobic digester; and
(g) recovering some or all of the residual fiber from the solid stream as a cellulosic fiber product.

Other variations provide a system for producing renewable biogas and cellulosic fiber from a cellulose-rich feedstock, the system comprising:
a vacuum steam-explosion vessel configured for receiving a cellulose-rich feedstock and water, mixing the cellulose-rich feedstock and the water, rapidly depressurizing via vacuum applied to the vacuum steam-explosion vessel, removing at least a portion of the water as extracted vapor out of the vacuum steam-explosion vessel via vacuum drying, thereby generating a first cellulose-rich intermediate stream;
a secondary separation vessel configured to receive the cellulose-rich intermediate stream and remove impurities present therein, thereby generating a second cellulose-rich intermediate stream;
an enzymatic-hydrolysis vessel configured to receive the second cellulose-rich intermediate stream and to hydrolyze the second cellulose-rich intermediate stream, under effective hydrolysis conditions and in the presence of cellulase enzymes, thereby generating low-viscosity cellulosic fibers comprising cellulose oligomers;
an anaerobic digester configured to receive the low-viscosity cellulosic fibers and ferment, under effective digestion conditions and in the presence of microorganisms, the low-viscosity cellulosic fibers to biomethane, thereby generating a biogas stream comprising the biomethane and a solid stream comprising residual fiber;
optionally, a recycle line configured to recycle a portion of the residual fiber to the enzymatic-hydrolysis vessel and/or to the anaerobic digester;
optionally, a dewatering unit configured to remove at least a portion of moisture present in the solid stream;
a system outlet configured for recovering the biogas stream as a biogas product; and
a system outlet configured for recovering the residual fiber as a fiber co-product.

BRIEF DESCRIPTION OF THE DRAWING

FIG. 1 is an exemplary block-flow diagram depicting some embodiments of the invention. FIG. 1 shows both an exemplary process for making biogas and a cellulose-fiber co-product, as well as an exemplary system configured to produce biogas and a cellulose-fiber co-product.

DETAILED DESCRIPTION OF EMBODIMENTS

The processes, methods, systems, apparatus, structures, and materials of the present invention will be described in detail by reference to various non-limiting embodiments.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with the accompanying drawing.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms, except in the case of a Markush group. Thus in some embodiments not otherwise explicitly recited, any instance of "comprising" may be replaced by "consisting of" or, alternatively, by "consisting essentially of."

Some variations of the invention are predicated on an optimized process designed to obtain a usable fiber material from waste cellulose-rich feedstocks while at the same time allowing the energy-efficient recovery of biogas with enhanced yield and rate. The recovered fiber co-product can be used for a variety of applications such as incorporation as a component in biocomposite materials, or pelletized or briquetted as a low-CI solid fuel, to name a few applications.

Cellulose-rich feedstocks may include means municipal solid waste (MSW), food waste, soiled paper, and agricultural residues such as wheat straw, sugarcane bagasse, rice straw, corn stover, beet pulp, cover-crop residues and meal, soy fibers and hulls, or similar residues produced during the harvesting or the processing of common agricultural commodities. Wood and wood residues are not preferred cellulose-rich feedstocks.

Some variations of the invention provide a process to produce renewable biogas and cellulosic fiber from a cellulose-rich feedstock, the process comprising:

(a) obtaining a cellulose-rich feedstock that is reduced in concentration of impurities, wherein the impurities comprise metals, plastics, glass, dirt, sand, and grit, and wherein the cellulose-rich feedstock is characterized by an average maximum length scale less than 5 inches;

(b) feeding the cellulose-rich feedstock and water to a vacuum steam-explosion vessel, wherein the cellulose-rich feedstock and the water are mixed within the vacuum steam-explosion vessel, wherein a rapid depressurization takes place via vacuum applied to the vacuum steam-explosion vessel, and wherein at least a portion of the water is removed as extracted vapor out of the vacuum steam-explosion vessel via vacuum drying, thereby generating a first cellulose-rich intermediate stream;

(c) feeding the cellulose-rich intermediate stream to a secondary separation vessel to remove at least 50 wt % of the remainder of the impurities present, thereby generating a second cellulose-rich intermediate stream;

(d) feeding the second cellulose-rich intermediate stream to an enzymatic-hydrolysis vessel operated under effective hydrolysis conditions and in the presence of cellulase enzymes to convert the second cellulose-rich intermediate stream to low-viscosity cellulosic fibers comprising cellulose oligomers;

(e) feeding the low-viscosity cellulosic fibers to an anaerobic digester operated under effective digestion conditions and in the presence of microorganisms capable of fermenting the low-viscosity cellulosic fibers to biomethane, thereby generating a biogas stream comprising the biomethane and a solid stream comprising residual fiber;

(f) optionally, recycling a portion of the residual fiber to the enzymatic-hydrolysis vessel and/or to the anaerobic digester; and (g) recovering some or all of the residual fiber from the solid stream as a co-product comprising the cellulosic fiber.

Biogas refers to a mixture of different gases produced by the breakdown of organic matter in the absence of oxygen. Biogas is a renewable energy source. The composition of biogas varies depending upon the substrate composition, as well as the conditions within the anaerobic reactor (temperature, pH, and substrate concentration). Biogas may contain at least 30, 35, 40, 45, 50, 55, 60, 65, 70, 75, or 80 vol % biomethane. Biogas typically also contains carbon dioxide, carbon monoxide, hydrogen, water, and nitrogen. The biomethane, carbon monoxide, and hydrogen molecules provide energy value to the biogas.

In some embodiments, step (a) comprises size reduction of the cellulose-rich feedstock.

In some embodiments, step (a) comprises removal metals from the cellulose-rich feedstock via magnetic separation and/or eddy-current separation.

In some embodiments, step (a) comprises optical screening to remove plastics from the cellulose-rich feedstock.

In some embodiments, step (a) comprises gravimetric screening to remove dirt, grit, and sand from the cellulose-rich feedstock.

In some embodiments, in step (b), the water is preheated prior to being added to the vacuum steam-explosion vessel.

The vacuum steam-explosion vessel may be a heated rotary reactor, for example. The vacuum steam-explosion vessel may contain an internal mixer. The vacuum steam-explosion vessel may be mixed via conveyance (e.g., internal agitation) of contents therein. The vacuum steam-explosion vessel may be mixed via rotation of the vacuum steam-explosion vessel. The vacuum steam-explosion vessel may be operated continuously, semi-continuously, or batchwise.

In some embodiments, the process further comprises removing contaminants from the extracted vapor, or a condensed form thereof, using activated carbon. In these or other embodiments, the process further comprises removing contaminants from the extracted vapor, or a condensed form thereof, using an absorption resin. The extracted vapor is removed out of the vacuum steam-explosion vessel during step (b).

In some embodiments, step (c) removes at least 75% of the remainder of the impurities present. In certain embodiments, step (c) removes at least 90% of the remainder of the impurities present.

In some embodiments, in step (d), the enzymatic-hydrolysis vessel is operated in the presence of lipase enzymes and/or amylase enzymes, in addition to the cellulase enzymes.

In some embodiments, in step (d), there is less than 10%, less than 5%, or less than 1% conversion of the second cellulose-rich intermediate stream to glucose. By limiting the enzymatic hydrolysis of the second cellulose-rich intermediate stream such that the hydrolysis does not significantly proceed all the way to glucose monomers, and makes cellulose oligomers instead, the fiber co-production potential is higher, and enzyme costs are reduced.

In some embodiments, the low-viscosity cellulosic fibers are characterized by a viscosity less than 10 Pa·s measured at a temperature of 25° C. and a moisture of 70 wt % $H_2O$.

In step (c), various types of anaerobic digesters may be employed. Anaerobic digesters can be designed and engineered to operate using a number of different configurations and can be categorized into batch vs. continuous process mode, mesophilic vs. thermophilic temperature conditions, high vs. low portion of solids, and single stage vs. multistage processes. In a batch system, biomass is added to the reactor at the start of the process. The reactor is then sealed for the duration of the process. In its simplest form batch processing needs inoculation with already processed material to start the anaerobic digestion. In continuous digestion processes, organic matter is constantly added or added in stages to the reactor. Here, the end products are constantly or periodically removed, resulting in constant production of biogas. Examples of this form of anaerobic digestion include continuous stirred-tank reactors, upflow anaerobic sludge blankets, expanded granular sludge beds, and internal circulation reactors.

The operational temperatures for anaerobic digesters determine the species of methanogens in the digesters. Mesophilic digestion takes place optimally around 30° C. to 38° C., or at ambient temperatures between 20° C. and 45° C., when mesophilic microorganisms are present. Thermophilic digestion takes place optimally around 50° C. to 60° C., or at elevated temperatures up to 70° C., when thermophilic microorganisms are present. In some embodiments, the digester(s) is/are operated at thermophilic temperature range (e.g., 50-60° C.) to enhance the disintegration and gas production of feedstock and the rate of this degradation.

The residence time in a digester varies with the amount and type of feed material and with the configuration of the digestion system. In a typical two-stage mesophilic digestion, residence time varies between 10 and 40 days, while for a single-stage thermophilic digestion, residence times is normally faster such as about 5 to 20 days.

High solids (dry) digesters are designed to process materials with a solids content between 25 and 40 wt %. Wet digesters can be designed to operate in either a high-solids content, with a total suspended solids concentration greater than 20 wt %, or a low-solids concentration less than 20 wt % (e.g., about 15 wt %).

This specification hereby incorporates by reference Taricska et al., "Anaerobic Digestion" In: *Biosolids Treatment Processes. Handbook of Environmental Engineering*, vol 6. Humana Press, 2007 for its teachings of the design and operation of anaerobic digesters, in some embodiments (without limitation).

In some embodiments, step (g) further comprises dewatering the solid stream to generate dirty water. Dewatering may utilize a centrifuge, a rotary vacuum system, a filter press, or a combination thereof, for example.

The dirty water may be treated in a wastewater treatment unit to generate wastewater discharge and cleaned water. In some embodiments, the wastewater treatment unit removes dissolved organic compounds. In some embodiments, the wastewater treatment unit removes dissolved perfluorinated and polyfluorinated substances (PFAS). In some embodiments, the wastewater treatment unit removes dissolved salts. The cleaned water may be fed back to the vacuum steam-explosion vessel as at least a portion of the water required in step (b), i.e., steam is made from the cleaned water for use in the vacuum steam-explosion vessel.

In certain embodiments, the cleaned water and a condensed form of the extracted vapor from step (b) are both fed to a water reservoir. Recycle water from the water reservoir may be fed back to the vacuum steam-explosion vessel as at least a portion of the water for the steam requirement in that vessel.

In some embodiments, the process further comprises combusting or partially oxidizing the biogas to generate renewable energy.

In some embodiments, the process further comprises combusting and biogas to generate heat, and using the heat to generate steam for powering a turbine to generate renewable electricity.

The cellulosic fiber co-product has many potential uses. In some embodiments, the process further comprises incorporating the cellulosic fiber in a biocomposite material. In these or other embodiments, the process further comprises incorporating the cellulosic fiber into a low-carbon-intensity solid-fuel pellet or briquette.

Some embodiments provide a process to produce renewable biogas and cellulosic fiber from a cellulose-rich feedstock, the process comprising:

obtaining a cellulose-rich feedstock characterized by an average maximum length scale less than 5 inches;

feeding the cellulose-rich feedstock and water to a vacuum steam-explosion vessel, wherein the cellulose-rich feedstock and the water are mixed within the vacuum steam-explosion vessel, wherein a rapid depressurization takes place via vacuum applied to the vacuum steam-explosion vessel, and wherein at least a portion of the water is removed as extracted vapor out of the vacuum steam-explosion vessel via vacuum drying, thereby generating a cellulose-rich intermediate stream;

feeding the cellulose-rich intermediate stream to an enzymatic-hydrolysis vessel operated under effective hydrolysis conditions and in the presence of cellulase enzymes to convert the cellulose-rich intermediate stream to low-viscosity cellulosic fibers comprising cellulose oligomers;

feeding the low-viscosity cellulosic fibers to an anaerobic digester operated under effective digestion conditions and in the presence of microorganisms capable of fermenting the low-viscosity cellulosic fibers to biomethane, thereby generating a biogas stream comprising the biomethane and a solid stream comprising residual fiber;

optionally, recycling a portion of the residual fiber to the enzymatic-hydrolysis vessel and/or to the anaerobic digester; and recovering some or all of the residual fiber from the solid stream as a co-product comprising the cellulosic fiber.

Other embodiments provide a process to produce cellulosic fiber from a cellulose-rich feedstock, the process comprising:

obtaining a cellulose-rich feedstock characterized by an average maximum length scale less than 5 inches;

feeding the cellulose-rich feedstock and water to a vacuum steam-explosion vessel, wherein the cellulose-rich feedstock and the water are mixed within the vacuum steam-explosion vessel, wherein a rapid depressurization takes place via vacuum applied to the vacuum steam-explosion vessel, and wherein at least a portion of the water is removed as extracted vapor out of the vacuum steam-explosion vessel via vacuum drying, thereby generating a cellulose-rich intermediate stream;

feeding the cellulose-rich intermediate stream to an enzymatic-hydrolysis vessel operated under effective hydrolysis conditions and in the presence of cellulase enzymes to convert the cellulose-rich intermediate stream to low-viscosity cellulosic fibers comprising cellulose oligomers;

separating the low-viscosity cellulosic fibers from a solid stream comprising residual fiber;

recovering the low-viscosity cellulosic fibers for storage or further use;

optionally, recycling a portion of the residual fiber to the enzymatic-hydrolysis vessel; and recovering some or all of the residual fiber from the solid stream as a co-product comprising the cellulosic fiber.

Other variations provide a cellulosic fiber product produced by a process comprising:

(a) obtaining a cellulose-rich feedstock that is reduced in concentration of impurities, wherein the impurities comprise metals, plastics, glass, dirt, sand, and grit, and wherein the cellulose-rich feedstock is characterized by an average maximum length scale less than 3 inches;

(b) feeding the cellulose-rich feedstock and water to a vacuum steam-explosion vessel, wherein the cellulose-rich feedstock and the water are mixed within the vacuum steam-explosion vessel, wherein a rapid depressurization takes place via vacuum applied to the vacuum steam-explosion vessel, and wherein at least a portion of the water is removed as extracted vapor out of the vacuum steam-explosion vessel via vacuum drying, thereby generating a first cellulose-rich intermediate stream;

(c) feeding the cellulose-rich intermediate stream to a secondary separation vessel to remove at least 50 wt % of the remainder of the impurities present, thereby generating a second cellulose-rich intermediate stream;

(d) feeding the second cellulose-rich intermediate stream to an enzymatic-hydrolysis vessel operated under effective hydrolysis conditions and in the presence of cellulase enzymes to convert the second cellulose-rich intermediate stream to low-viscosity cellulosic fibers comprising cellulose oligomers;

(e) feeding the low-viscosity cellulosic fibers to an anaerobic digester operated under effective digestion conditions and in the presence of microorganisms capable of fermenting the low-viscosity cellulosic fibers to biomethane, thereby generating a biogas stream comprising the biomethane and a solid stream comprising residual fiber;

(f) optionally, recycling a portion of the residual fiber to the enzymatic-hydrolysis vessel and/or to the anaerobic digester; and (g) recovering some or all of the residual fiber from the solid stream as a cellulosic fiber product.

Other variations provide a system for producing renewable biogas and cellulosic fiber from a cellulose-rich feedstock, the system comprising:

a vacuum steam-explosion vessel configured for receiving a cellulose-rich feedstock and water, mixing the cellulose-rich feedstock and the water, rapidly depressurizing via vacuum applied to the vacuum steam-explosion vessel, removing at least a portion of the water as extracted vapor out of the vacuum steam-explosion vessel via vacuum drying, thereby generating a first cellulose-rich intermediate stream;

a secondary separation vessel configured to receive the cellulose-rich intermediate stream and remove impurities present therein, thereby generating a second cellulose-rich intermediate stream;

an enzymatic-hydrolysis vessel configured to receive the second cellulose-rich intermediate stream and to hydrolyze the second cellulose-rich intermediate stream, under effective hydrolysis conditions and in the presence of cellulase enzymes, thereby generating low-viscosity cellulosic fibers comprising cellulose oligomers;

an anaerobic digester configured to receive the low-viscosity cellulosic fibers and ferment, under effective digestion conditions and in the presence of microorganisms, the low-viscosity cellulosic fibers to biomethane, thereby generating a biogas stream comprising the biomethane and a solid stream comprising residual fiber;

optionally, a recycle line configured to recycle a portion of the residual fiber to the enzymatic-hydrolysis vessel and/or to the anaerobic digester;

optionally, a dewatering unit configured to remove at least a portion of moisture present in the solid stream;

a system outlet configured for recovering the biogas stream as a biogas product; and a system outlet configured for recovering the residual fiber as a fiber co-product.

FIG. 1 is an exemplary block-flow diagram depicting some embodiments of the invention. The following non-limiting description makes reference to the accompanying drawing (FIG. 1), as well as designations of various process and system embodiments in FIG. 1. In FIG. 1, one or more steps or unit operations may optionally be omitted, without departing from the spirit and principles of the present disclosure. Also, additional steps or unit operations may optionally be added, without departing from the spirit and principles of the present disclosure.

When FIG. 1 is describing a process 100, the boxes labeled 1, 2, 3, . . . , 9 are in reference to process steps. When FIG. 1 is describing a system 100, the labeled boxes are in reference to unit operations and apparatus.

Step 1: Primary Sorting and Coarse Size Reduction.

In this step (101), extraneous materials and a significant amount of non-cellulose-rich materials are removed from the feedstock. The size reduction is coarse, typically not below several inches of a characteristic dimension unless the material is already procured with a smaller size. In the case of MSW, this step may include a variety of sub-steps, such as: (i) magnet and eddy current separation to remove ferrous and non-ferrous metals, respectively; (ii) optical screening to remove recyclable plastics; and (iii) gravimetric screening to remove dirt, grit, sand, stones, and glass. Only a gravimetric screen to remove dirt, grit, sand, and stones may be necessary for an agricultural waste stream, since typically agricultural wastes do not contain large quantities of metals in bulk form (metals are usually only contained in the biomass structure itself, and at very low concentrations).

Step 2: Vacuum Steam Expansion.

The prescreened material is fed into a vacuum steam-explosion vessel (102) comprising an externally heated vessel whose contents are mixed by an internal mixer, conveyance, rotation of the vessel, or a combination thereof. The vessel contents are mixed throughout the reactor operations, whether batch, continuous, or semi-batch.

The vacuum steam-explosion vessel 102 may be a BurCell® system, such as a BurCell® Heater Rotary Reactor or a similarly designed device. In embodiments employing a BurCell® system, reference is made to U.S. Pat. No. 11,458,414, issued on Oct. 4, 2022; U.S. Pat. No. 8,034,132, issued on Oct. 11, 2011; U.S. Pat. No. 7,497,392, issued on Mar. 3, 2009; and Emerson et al., "Chemical Characterization and Conversion Assessment of BurCell® System Treated MSW Materials", Idaho National Laboratory, CRADA No. 17-CR-01, Report No. INL/EXT-17-43190, September 2017, each of which is hereby incorporated by reference.

With continued reference to FIG. 1, the reactor operations may consist of the following substeps. The "reactor" is synonymous with the vacuum steam-explosion vessel 102.

In substep 2(a), a controlled amount of cellulose-rich material is fed into the vessel.

In substep 2(b), water is added in a controlled ratio with the cellulose-rich material. The water is typically preheated.

In substep 2(c), while the vessel is heated, a rapid depressurization is imposed inside the vessel by an external vacuum system. The vacuum can be kept for a period. Then, the pressure is allowed to normalize according to the temperature, reaching the saturation temperature of water vapor at the desired pressure. Temperature control is achieved by pressure control, while the external heat source controls the heating rate.

In substep 2(d), after the feedstock is kept at the desired temperature and pressure for the prescribed time, the vacuum system extracts vapor from the vessel. As the vessel heating is maintained, the moisture level of the processed material is controlled as more water is evaporated and extracted; thus, during this substep, the vessel operates as a vacuum dryer.

In substep 2(e), once the desired amount of water has been removed, and the moisture level of the reactor hold-up has reached the desired target, the vacuum system is disengaged, and the vessel is allowed to normalize to atmospheric pressure.

In substep 2(f), a vapor recovery system (110) is utilized. The extracted vapor (primarily steam) is condensed, and the condensate is returned to a hold-up tank and stored for reuse. As the evaporation in the vessel may remove low-boiling volatile organic contaminants (VOCs) present in the feedstock, the aqueous stream leaving the vessel may be appropriately treated to remove such contaminants. For example, the condensate stream may be passed through an activated carbon bed where the organic contaminants are removed by absorption. Also, some PFAS are volatile at the vessel's operating conditions and may be removed from the water stream by absorption on special resins after condensation. The removal of contaminants is not limited to the liquid phase. For example, removal of contaminants may be carried out in the vapor phase by selective adsorption of dissolved organic molecules on resins.

In substep 2(g), upon completion of the pretreatment, the material is discharged.

Step 3: Secondary Separation.

The discharged material is subjected to final screening in step 103, typically to remove non-organic material whose separation is easier now that most of the cellulosic material has been homogenized into a pulp or fluff-like material or separated organics. Such material may be sand, grits, and small residual metallic, plastic, and glass fragments.

Step 4: Enzymatic Hydrolysis.

The separated organics are fed into a hydrolysis vessel (104), such as a stirred tank, a hydro pulper, or an extruder where under controlled moisture level and pH, enzymes are added to reduce viscosity and convert long cellulose molecules into oligomers (e.g., oligomers with an average degree of polymerization from about 2 to about 100). Enzymes used are mainly cellulases which can be combined with lipases, amylases, and/or other enzymes to obtain the desired hydrolytic action.

Step 5: Anaerobic Digestion.

The hydrolyzed, highly bioavailable, and low-viscosity feedstock is fed into an anaerobic digester (105) where biogas is generated under anaerobic conditions. The extent and duration of this step are preferably based on the desired gas production and characteristics of the residual fibers to be recovered. The biogas is removed from the digester 105 for further processing or utilization. The residual material, from which biogas has been removed, in referred to as digestate.

Step 6: Fiber Separation.

After digestion, a fiber separator (106) removes a fiber fraction from the digestate. The fiber fraction may be recycled to the hydrolysis vessel to enhance biogas recovery by increased hydrolysis (oligomer generation). Alternatively, or additionally, the fiber fraction may be recycled to the digester 105 to control the solid amount and retention time in the digester, thus decoupling solid retention time from hydraulic retention time. Alternatively, or additionally, a targeted residual co-product can be obtained with desired characteristics by recycling none or only some of the cellulosic fiber.

Step 7: Mechanical Dewatering.

The digestate is mechanically dewatered (107) using common devices such as centrifuges, rotary vacuum screens, filter presses, etc., preferably until surface water is absent. The dewatered material is ready for final disposition and additional processing, while the water is recycled after appropriate treatment.

Step 8: Water Treatment.

Water treatment (108) ensures that before the water is recycled into the process, adequate steps are taken to (a) remove any organic compounds, including dissolved PFAS; (b) remove and control the number of dissolved salts—particularly chlorides—via precipitation and purging; and (c) receive and treat fresh water as needed to compensate for water losses in the process.

Step 9: Water Reservoir.

A water reservoir (109) is used to collect condensate and treated recycled water. In addition, the reservoir provides water to the vacuum steam explosion and anaerobic digestion processes.

Step 10: Steam Recovery.

In a steam-recovery step (110), extracted vapor (primarily steam), from the vacuum steam-explosion vessel 102, is condensed. The condensate is returned to a hold-up tank and stored for reuse. The hold-up tank may be the water reservoir 109, or another tank.

The recited process options and process embodiments may be utilized entirely or partially. Some embodiments may omit process steps. Some embodiments include other process steps that are not explicitly taught herein but are conventional in the chemical-engineering and biorefinery arts. In preferred embodiments, a combination of process options and process embodiments is configured to optimize overall biogas products and/or production of co-products.

The biogas may be stored, sold, used, further treated, or otherwise handled. Certain uses of the biogas include use as a fuel in gas engines or gas turbines to generate electric and thermal power; compression or liquefaction to produce renewable natural gas (RNG) in the form of compressed natural gas or liquefied natural; conversion to dimethyl ether (DME) for fuel use or chemical conversion of DME to other products.

The cellulosic fiber co-product, or a derivative thereof, may be used in a biocomposite material. For example, the cellulosic fiber co-product may be combined with polyethylene, polypropylene, polyethylene terephthalate, polylactide, polyhydroxyalkanoate, starch, polyalkylene furanoates such as polyethylene furanoate, and many others. Optionally, the particle size of the cellulosic fiber co-product is reduced prior to incorporation into a biocomposite material. Optionally, there is a surface modification (e.g., via functional groups) of the cellulosic fiber co-product to incorporation into a biocomposite material The cellulosic fiber co-product, or a derivative thereof, may be used as a low-carbon-intensity (low-CI) solid fuel, such as in the form of powder, pellets, or briquettes. Optionally, other solid materials with fuel value are added to the cellulosic fiber co-product, such as (but not limited to) lignin, waste sugars, raw biomass, pretreated biomass, and so on.

The cellulosic fiber co-product, or a derivative thereof, may be used as a low-carbon-intensity (low-CI) gasification feedstock for making syngas. Optionally, other solid materials with syngas potential are added to the cellulosic fiber co-product, such as (but not limited to) lignin, waste sugars, raw biomass, pretreated biomass, and so on. Syngas produced from the low-CI cellulosic fiber co-product has a vast number of uses, as is well-known.

Many other uses of the cellulosic fiber co-product exist, as will be appreciated by a person skilled in the art. To name just a few, the cellulosic fiber co-product may be applied as a soil conditioner, used as agricultural fertilizer, used in composting such as a base material for an organic soil product, applied to a brownfield as a soil enhancement material, or employed as a landfill conditioner (cover material), for example.

In this detailed description, reference has been made to multiple embodiments and to the accompanying drawing(s) in which are shown by way of illustration specific exemplary embodiments of the invention. These embodiments are described in sufficient detail to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein. This disclosure hereby incorporates by reference U.S. Pat. No. 11,458,414, issued on Oct. 4, 2022; U.S. Pat. No. 8,034,132, issued on Oct. 11, 2011; and U.S. Pat. No. 7,497,392, issued on Mar. 3, 2009.

The embodiments, variations, and FIGURE described above should provide an indication of the utility and versatility of the present invention. Other embodiments that do not provide all of the features and advantages set forth herein may also be utilized, without departing from the spirit and scope of the present invention. Such modifications and variations are considered to be within the scope of the invention defined by the claims.

What is claimed is:

1. A process to produce renewable biogas and cellulosic fiber from a cellulose-rich feedstock, said process comprising:
    (a) obtaining a starting cellulose-containing feedstock and removing impurities to generate a cellulose-rich feedstock that is reduced in concentration of said impurities compared to said starting cellulose-containing feedstock, wherein said impurities comprise metals, plastics, glass, dirt, sand, and grit, and wherein said cellulose-rich feedstock is characterized by an average maximum length scale less than 5 inches;
    (b) feeding said cellulose-rich feedstock and starting water to a vacuum steam-explosion vessel, wherein said cellulose-rich feedstock and said starting water are mixed within said vacuum steam-explosion vessel, wherein a rapid depressurization takes place via vacuum applied to said vacuum steam-explosion vessel, and wherein water is removed as extracted vapor out of said vacuum steam-explosion vessel via vacuum drying, thereby generating a first cellulose-rich intermediate stream;
    (c) feeding said cellulose-rich intermediate stream to a secondary separation vessel to remove at least 50 wt % of the remainder of said impurities present, thereby generating a second cellulose-rich intermediate stream;
    (d) feeding said second cellulose-rich intermediate stream to an enzymatic-hydrolysis vessel operated in the presence of cellulase enzymes to convert said second cellulose-rich intermediate stream to low-viscosity cellulosic fibers comprising cellulose oligomers;
    (e) feeding said low-viscosity cellulosic fibers to an anaerobic digester operated in the presence of microorganisms capable of fermenting said low-viscosity cellulosic fibers to biomethane, thereby generating a biogas stream comprising said biomethane and a solid stream comprising residual fiber;
    (f) optionally, recycling said residual fiber to said enzymatic-hydrolysis vessel and/or to said anaerobic digester; and
    (g) recovering said residual fiber from said solid stream as a co-product comprising said cellulosic fiber.

2. The process of claim 1, wherein step (a) comprises size reduction of said cellulose-rich feedstock.

3. The process of claim 1, wherein step (a) comprises removal metals from said cellulose-rich feedstock via magnetic separation and/or eddy-current separation.

4. The process of claim 1, wherein step (a) comprises optical screening to remove plastics from said cellulose-rich feedstock.

5. The process of claim 1, wherein step (a) comprises gravimetric screening to remove dirt, grit, and sand from said cellulose-rich feedstock.

6. The process of claim 1, wherein said vacuum steam-explosion vessel is a heated rotary reactor.

7. The process of claim 1, wherein in step (b), said water is preheated prior to being added to said vacuum steam-explosion vessel.

8. The process of claim 1, wherein said vacuum steam-explosion vessel contains an internal mixer.

9. The process of claim 1, wherein said vacuum steam-explosion vessel is mixed via conveyance of contents therein.

10. The process of claim 1, wherein said vacuum steam-explosion vessel is mixed via rotation of said vacuum steam-explosion vessel.

11. The process of claim 1, wherein said vacuum steam-explosion vessel is operated continuously or semi-continuously.

12. The process of claim 1, wherein said vacuum steam-explosion vessel is operated batch-wise.

13. The process of claim 1, said process further comprising removing contaminants from said extracted vapor, or a condensed form thereof, using activated carbon.

14. The process of claim 1, said process further comprising removing contaminants from said extracted vapor, or a condensed form thereof, using an absorption resin.

15. The process of claim 1, wherein step (c) removes at least 75% of said remainder of said impurities present.

16. The process of claim 1, wherein step (c) removes at least 90% of said remainder of said impurities present.

17. The process of claim 1, wherein in step (d), said enzymatic-hydrolysis vessel is operated in the presence of lipase enzymes and/or amylase enzymes, in addition to said cellulase enzymes.

18. The process of claim 1, wherein in step (d), there is less than 10% conversion of said second cellulose-rich intermediate stream to glucose.

19. The process of claim 1, wherein in step (d), there is less than 5% conversion of said second cellulose-rich intermediate stream to glucose.

20. The process of claim 1, wherein in step (d), there is less than 1% conversion of said second cellulose-rich intermediate stream to glucose.

21. The process of claim 1, wherein said low-viscosity cellulosic fibers are characterized by a viscosity less than 10 Pascal-seconds measured at a temperature of 25° C. and a moisture of 70 wt % $H_2O$.

22. The process of claim 1, wherein step (g) further comprises dewatering said solid stream to generate dirty water.

23. The process of claim 22, wherein said dewatering utilizes a centrifuge.

24. The process of claim 22, wherein said dewatering utilizes a rotary vacuum system.

25. The process of claim 22, wherein said dewatering utilizes a filter press.

26. The process of claim 22, wherein said dirty water is treated in a wastewater treatment unit to generate wastewater discharge and cleaned water.

27. The process of claim 26, wherein said wastewater treatment unit removes dissolved organic compounds.

28. The process of claim 26, wherein said wastewater treatment unit removes dissolved perfluorinated and polyfluorinated substances.

29. The process of claim 26, wherein said wastewater treatment unit removes dissolved salts.

30. The process of claim 26, wherein said cleaned water is fed back to said vacuum steam-explosion vessel as at least a portion of said water.

31. The process of claim 26, wherein said cleaned water and a condensed form of said extracted vapor from step (b) are both fed to a water reservoir.

32. The process of claim 31, wherein recycle water from said water reservoir is fed back to said vacuum steam-explosion vessel as at least a portion of said water.

33. The process of claim 1, said process further comprising combusting or partially oxidizing said biogas to generate renewable energy.

34. The process of claim 1, said process further comprising combusting said biogas to generate heat, and using said heat to generate steam for powering a turbine to generate renewable electricity.

35. The process of claim 1, said process further comprising incorporating said cellulosic fiber in a biocomposite material.

36. The process of claim 1, said process further comprising incorporating said cellulosic fiber into a low-carbon-intensity solid-fuel pellet or briquette.

* * * * *